(12) United States Patent
Castino et al.

(10) Patent No.: US 6,177,019 B1
(45) Date of Patent: Jan. 23, 2001

(54) METHOD AND APPARATUS FOR REMOVING TUMOR CELLS FROM TUMOR CELL-CONTAMINATED STEM CELL PRODUCTS

(75) Inventors: Franco Castino, Sudbury; Sumith R. Wickramasinghe, Marlborough, both of MA (US)

(73) Assignee: HemaSure Inc., Marlborough, MA (US)

(*) Notice: Under 35 U.S.C. 154(b), the term of this patent shall be extended for 0 days.

(21) Appl. No.: 09/242,857

(22) PCT Filed: Aug. 22, 1997

(86) PCT No.: PCT/US97/14774
  § 371 Date: Feb. 24, 1999
  § 102(e) Date: Feb. 24, 1999

(87) PCT Pub. No.: WO98/08556
  PCT Pub. Date: Mar. 5, 1998

Related U.S. Application Data (60) Provisional application No. 60/034,758, filed on Jan. 6, 1997, and provisional application No. 60/024,536, filed on Aug. 26, 1996.

(51) Int. Cl.[7] ............................. B01D 37/00; B01D 29/00
(52) U.S. Cl. ........................... 210/767; 210/435; 210/436; 210/472; 210/483; 210/488; 210/489; 210/503; 210/504; 210/505; 210/506; 210/507; 210/508; 435/2
(58) Field of Search ................... 210/435, 436, 210/472, 483, 488, 489, 490, 491, 503, 504, 505, 506, 507, 508, 650, 651, 767; 422/101; 436/177, 178; 435/2

(56) References Cited

U.S. PATENT DOCUMENTS

| | | | |
|---|---|---|---|
| 4,761,366 | 8/1988 | Nakajima et al. | 435/2 |
| 4,816,409 | 3/1989 | Tanaka et al. | 435/311 |
| 4,880,548 | * 11/1989 | Pall et al. | 210/767 |
| 5,190,657 | 3/1993 | Heagle et al. | 210/645 |
| 5,403,917 | 4/1995 | Boos et al. | 530/351 |

OTHER PUBLICATIONS

Gudemann, C. et al., "0116 Intraoperative Autotransfusion in Urologic Cancer Surgery by Using Membrane Filters," XXIIIrd Congress of the ISBT, Abstracts in Vox Sang, 67(S2):22.

Osawa, T. et al., "Intraoperative Blood Recovery in Transurethral Resection of Prostate (TURP)," *Nippon–Hinyokika Gakkai–Zasshi*, 83(8):1276–83 (1992).

Miller, G.V. et al., "Autologous Transfusion: An Alternative to Transfusion with Banked Blood During Surgery for Cancer," *Br. J. Surg.*, 78:713–15 (1981).

Trickett A.E., "Tumour Cell Purging for Autologous Bone Marrow Transplantation," *Medical Laboratory Sciences*, 47:120–31 (1990).

Ross, A.A. et al., "Detection and Viability of Tumor Cells in Peripheral Blood Stem Cell Collections From Breast Cancer Patients Using Immunocytochemical and Clonogenic Assay Techniques," *Blood*, 82(9):2605–10 (1993).

Moss, T.J. et al., "The Risk of Tumor Cell Contamination in Peripheral Blood Stem Cell Collections," *Journal of Hematotherapy*, 1:225–32 (1992).

Brugger, W. et al., "Mobilization of Tumor Cells and Hematopoietic Progenitor Cells into Peripheral Blood of Patients with Solid Tumors," *Blood*, 83(3):636–40 (1994).

* cited by examiner

*Primary Examiner*—John Kim
(74) *Attorney, Agent, or Firm*—Heslin & Rothenberg, P.C.

(57) ABSTRACT

A method for removing tumor cells from tumor cell-contaminated stem cell products is disclosed. One embodiment of the method relies on an in-line filtration device that includes a tumor cell reduction filter means, preferably comprised of one or more tumor cell reduction filter pads. The tumor cell reduction filter means provides at least a ten-fold reduction in tumor cells while allowing for at least a 30% recovery of stem cells in a filtered stem cell product.

20 Claims, 4 Drawing Sheets figure 1 figure 2 figure 3b figure 3a figure 4

METHOD AND APPARATUS FOR REMOVING TUMOR CELLS FROM TUMOR CELL-CONTAMINATED STEM CELL PRODUCTS

CROSS REFERENCE TO RELATED APPLICATIONS

This application is filed under 35 U.S.C. §371 and is derived from International Patent Application Number PCT/US97/14774, filed Aug. 22, 1997, which claims the priority of U.S. Provisional Patent Application Serial No. 60/034,758, filed Jan. 6, 1997 and 60/024,536, filed Aug. 26, 1996, the disclosures of which are hereby incorporated by reference.

FIELD OF THE INVENTION

The invention relates to the filtration of blood cells and more specifically, to a method for selectively removing tumor cells from tumor cell-contaminated stem cell products. A preferred embodiment of the invention provides a method which relies on an in-line filtration device that includes one or more tumor cell reduction filter pads.

BACKGROUND OF THE INVENTION

Hematopoietic cells are rare, pluripotent cells, having the capacity to give rise to all lineages of blood cells. Through a process referred to as commitment, self-renewing stem cells are transformed into progenitor cells which are the precursors of several different blood cell types, including erythroblasts, myeloblasts and monocyte/macrophages. Due to their self-renewing capacity, stem cells have a wide range of potential applications in transfusion medicine, and in particular, in the autologous support of cancer patients.

Procedures have been developed whereby stem cells can be obtained from a donor, stored and later transplanted into a patient experiencing an immunosuppressive condition, such as following high dose chemotherapy or total body radiation. In the past, stem cells were harvested from bone marrow in a costly and painful procedure which required hospitalization and general anesthesia. New developments in technology, however, now make it possible to derive stem cells and committed progenitor cells from peripheral blood. Collection of stem cell products (SC products), a term which includes both true stem cells and committed progenitor cells (i.e., CD 34$^+$cells are included), can thus be done on an outpatient basis, eliminating the need for hospitalization. In addition, stem cell products can also be derived from peripheral blood during elective surgeries.

Once collected, the SC products, whether from bone marrow or peripheral blood, can be stored for future use, one of the most significant of which is transplantation to enhance hematologic recovery following an immunosuppressive procedure such as chemotherapy.

There is, however, one significant drawback to the use of this very beneficial reinfusion procedure. Inevitably, when SC products are obtained from a cancer patient, a significant number of tumor cells will also be collected, thereby contaminating the SC product. Subsequently, when the SC product is reinfused into the patient, the tumor cells are also reintroduced, increasing the concentration of tumor cells in the patient's blood stream. While circulating tumor cells have not been directly linked to the relapse of a particular cancer, in the case of lymphoma, for example, reinfused cells have been traced to sites of disease relapse. In cases involving adenocarcinoma, it has been estimated that for a 50 kilogram adult, approximately 150,000 tumor cells can be reinfused during a single stem cell transplantation. Moreover, it has been shown that the tumor cells present in the SC product are viable and capable of in vitro clonogenic growth, thus suggesting that they could indeed contribute to post-reinfusion relapse. Ovarian cancer cells, testicular cancer cells, breast cancer cells, multiple myeloma cells, non-Hodgkin's lymphoma cells, chronic myelogenous leukemia cells, chronic lymplocytic leukemia cells, acute myeloid leukemia cells, and acute lymphocytic leukemia cells are known to be transplantable.

The extent of tumor cell contamination of SC products appears to vary greatly from patient to patient, and values within the range of 11 to 78 percent have been recorded. Therefore, as the reinfusion of circulating tumor cells may well circumvent the benefits provided by aggressive chemotherapy followed by stem cell transplantation, the development of techniques that effectively remove tumor cells from SC products will significantly further the widespread use of a very beneficial and valuable clinical procedure.

Methods currently used to separate the valuable stem cells from the undesired tumor cell-contaminated product rely on a positive selection technique that identifies stem cells and progenitor cells that express markers for the CD34$^+$antigen and remove them from the contaminated product. These methods are very labor intensive and require the use of specialized equipment, thus greatly increasing the cost of patient care and severely limiting the use of SC products in transplantation procedures.

An alternative to positive selection for removal of tumor cells from blood was provided by Gudemann et al., who described filtration with special leukocyte depletion membrane filters (which work by adsorbing charged particles) to remove urologic tumor cells from autologous blood during an intraoperative mechanical autotransfusion (IAT) procedure. (Gudemann, C., Wiesel, M. and Staehler, G., *Intraoperative Autotransfusion In Urologic Cancer Surgery By Using Membrane Filters*, XXIII$^{rd}$ Congress of the ISBT, abstracts in Vox Sang., 67 (S2), 22.) A disadvantage of the membrane filters used by Gudemann el al is that they do not selectively retain tumor cells. White blood cells, including stem cells, are also retained. Thus, tumor cells are not removed from stem cells.

The work of Miller et al also teaches that standard blood transfusion filters are ineffective at removing tumor cells from autologous blood. (Miller, G. V., Ramsden, C. W. and Primrose, J. N., *Autologous transfusion: an alternative to transfusion with banked blood during surgery for cancer*, B. J. Surg. 1991, Vol. 78, Jun., 713–715).

It is therefore desirable, based upon the valuable benefits achieved by the transplantation of previously obtained stem cell products, benefits that ultimately result in increased survival rates, to provide a low-cost, clinically effective method for the selective removal of tumor cells from tumor cell-contaminated stein cell products.

SUMMARY OF THE INVENTION

The present invention provides a low-cost, clinically effective method for selectively removing tumor cells from a tumor cell-contaminated stem cell (TCCSC) product while allowing for optimal recovery of hematopoietic stem cells and committed progenitor cells.

Thus, one aspect of the invention is a method for removing tumor cells from a tumor cell-contaminated stem cell product, comprising the steps of:

(a) providing an in-line filtration device including:

a housing having an inlet port and an outlet port therein; and a tumor cell reduction filter means disposed within said housing between the inlet port and the outlet port so as to filter tumor cell-contaminated stem cell products which flow into the filtration device via the inlet port, said tumor cell reduction filter means dividing said housing into a first chamber and a second chamber;

(b) providing a tumor cell-contaminated stein cell product;

(c) passing the tumor cell-contaminated stem cell product through the filtration device wherein tumor cells are retained by the tumor cell reduction filter means within the filtration device and the stem cell product passes through the tumor cell reduction filter means and out of the filtration device; and (d) recovering a tumor cell-depleted stem cell product.

Preferably, the tumor cell reduction filter means provides at least a 10-fold unit reduction in tumor cells and at least a 30% recovery (more preferably a 50% recovery) of stem cells in the tumor-cell depleted stem cell product, and the flow rate of stem cell product through the filter means will be at least 50 mL per hour. To provide optimal tumor cell retention and stem cell recovery, the filter means has an air permeability of at least about 750 L/min to about $1 \times 10^4$ L/min.

Thus, one embodiment of the invention provides a device suitable for use as a tumor cell reduction filter means in an in-line filtration device wherein the tumor cell reduction filter means provides at least a ten-fold reduction in tumor cells and at least a 30% recovery of stem cells in a filtered stem cell product. Preferably the tumor cell reduction filter means provides a stein cell product flow rate of at least 50 mL per hour and has an air permeability of at least about 750 Lmin to about $1 \times 10^4$ L/min, preferably about $3.3 \times 10^3$ L/min.

Tumor cell reduction filter means encompass any sort of device or mechanically stable substrate that relies on size as the basis for distinguishing whether particulate matter in a fluid milieu will be passed or retained. The filter means may additionally have surface chemistry adapted to facilitate distinguishing between passage or retention. Examples of the several types of filter means include, but are not limited to, polymer membranes having defined pore size, non-woven textile pads, fiber pads, aerogels and the like. One may also consider as appropriate filter means certain classes of hydrogels, particularly those attached to a composite material for mechanical stability.

Another embodiment of the invention is an apparatus suitable for use as a filtration device for removing tumor cells from tumor cell-contaminated stem cell products comprising:

a housing having an inlet port and an outlet port therein; and a tumor cell reduction filter means disposed within said housing between the inlet port and outlet port so as to filter tumor cell-contaminated stem cell products which flow into the housing via the inlet port, said tumor cell reduction filter means dividing said housing into a first chamber and a second chamber.

According to the principles of the many aspects and embodiments of the present invention, the tumor cell reduction filter means may be one or more tumor cell reduction filter (TCRF) pads having a shape-sustaining web matrix construction comprised of a plurality of fibers and fibrils. Optimally, the fibers are comprised of polyester having a denier of about 1.5 mm and the fibrils are comprised of cellulose. As tumor cells are larger than stem cells, the tumor cell reduction filter pads will selectively retain tumor cells while allowing the smaller stein cells to pass through for recovery.

The method of the invention is suited to removing tumor cells from tumor cell-contaminated stem cell products contaminated with tumor cells such as ovarian cancer cells, testicular cancer cells, breast cancer cells, multiple myeloma cells, non-Hodgkin's lymphoma cells, chronic myelogenous leukemia cells, chronic lymphocytic leukemia cells, acute myeloid leukemia cells, and acute lymphocytic leukemia cells. In particular, the tumor cell-contaminated stem cell product may be a stem cell product contaminated with ductal carcinoma cells or adenocarcinoma cells.

The present invention thus provides both therapeutic and diagnostic advantages. By removing tumor cells from the contaminated product, the method not only provides a supply of tumor cell-depleted stem cells for transplantation, it also provides a diagnostic tool for determining the concentration of tumor cells in circulating blood.

Typically, the concentration of tumor cells in circulating blood is exceedingly low (from 4 to 5600 per $1.6 \times 10^8$ mononuclear cells), and it is therefore extremely difficult to obtain an accurate count. According to the principles of the present invention, following the filtration of a known volume of blood product, tumor cells will be retained within the TCRF pad. These cells can then be counted in situ or they can be recovered, by means such as backwashing the TCRF pad with saline, and counted, by means such as flow cytometry or spectrometry. As the original volume of blood product was known, the concentration of tumor cells in that volume can then be calculated, based upon the volume of tumor cells retained by the TCRF pad.

Depth filtration of cell suspensions is a well-known separation technique for the leukodepletion of red blood cell concentrates and is a function of two mechanisms, sieving and adhesion. Sieving is caused by the mechanical entrapment of larger cells within the matrix of the filter pad, while adhesion is caused by the interaction of blood cell surfaces and the filter pad material. In leukocyte filtration, it is believed that more leukocytes are retained by the effects of adhesion than by sieving. Generally, depth filtration filter pads are comprised of a plurality of fibers and fibrils that are entwined into a web matrix that provides for increased particle attachment. Depth filtration is thus distinguished from surface filtration, where the full extent of particle attachment occurs on the surface of the filter pad.

Existing methods of removing tumor cells from contaminated stem cell products rely on positive selection techniques and require very expensive, specialized equipment and significant operator time. In contrast, the principles of the present invention involve a low-cost, easy-to-use, in-line depth filtration device that includes a tumor cell reduction filter means. It can be gravity-driven or pumped.

The in-line filtration device comprises a housing having an inlet port and an outlet port therein, a TCRF means disposed within the housing between the inlet port and outlet port so as to filter the TCCSC product that flows into the filtration device via the inlet port. The TCRF means divides the housing into a first chamber capable of collecting and directing the flow of unfiltered liquid therein and a second chamber in fluid flow relationship with the first chamber capable of collecting and directing the flow of filtered liquid.

Preferably, the filtration device will include means within the filtration device, for allowing gases such as air to vent from the filtration device through the outlet port during filtration. The filtration device may be sized so that the distance between the TCRF means and the inlet port prevents the accumulation of gases in the first chamber. Similarly, the filtration device may be sized so that the distance between the TCRF means and the outlet port forces gases within the second chamber to enter the outlet port during filtration.

Preferably, the means, disposed within the device, for allowing gases to vent through the filtration device through the outlet port during filtration comprises a flow deflector disposed within the second chamber between the TCRF means and the outlet port. The flow deflector may comprise a relatively flat member such as a disk, and the disk may comprise at least one radially extending rib.

The filtration device may include one or more TCRF pads as the filtration means, and a seal ring may be mounted between two of the TCRF pads. The inlet port and outlet port of the filtration device may be coaxially oriented. The housing may comprise an inlet section and an outlet section attached to the inlet section. The inlet port may be disposed within the inlet section and the outlet port may be disposed within the outlet section. The one or more TCRF pads may be sealed between the inlet section and either the outlet section or a seal ring. If the device contains a plurality of TCRF pads, the pads may be stacked one on top of the other and be separated about their periphery by seal rings.

Although this invention is susceptible to embodiment in many different forms, preferred embodiments of the invention are shown. It should be understood, however, that the present disclosure is to be considered as a exemplification of the principles of this invention and is not intended to limit the invention to the embodiments illustrated.

BRIEF DESCRIPTION OF THE DRAWINGS

Numerous other advantages and features of the present invention will become readily apparent from the following detailed description of the preferred embodiment, the appended claims and the accompanying drawings wherein:

DETAILED DESCRIPTION OF THE PREFERRED EMBODIMENT

A preferred embodiment of the present invention relies on an in-line gravity driven filtration device that includes a tumor cell reduction filter (TCRF) means that is most preferably comprised of one or more TCRF pads. A TCRF pad has a shape-sustaining web matrix construction formed from a plurality of fibers and fibrils and are especially well suited for the selective removal of tumor cells (TC), including, for example, lung carcinoma cells, lymphatic system carcinoma cells, ovarian carcinoma cells, testicular carcinoma cells, ductal carcinoma cells, mammary carcinoma cells and adenocarcinoma cells, from a tumor cell-contaminated stem cell (TCCSC) product.

As referred to herein, the terms upstream, top or tip refers to a location of the flow of TCCSC product prior to filtration through the TCRF means within the filtration device. Conversely, the terms downstream, bottom or down as used herein refers to a location of the flow of filtered stem cell (FSC) product, following filtration through the TCRF means within the filtration device. Moreover, as used herein, the terms radially and axially refer to the radial and axial directions, respectively, relative to axis A—A of FIG. 2, running lengthwise through the center of the filtration device.

Although various embodiments of the filtration device may be used to practice the method of the present invention, each embodiment comprises a housing typically formed by an inlet section, an outlet section, a TCRF means, and means for allowing gases to vent from the filtration device through an outlet port. The device preferably will include means to enable air within the filtration device to vent downstream without manipulation of various components, the use of vent filters or other external means. Preferably, the device will incorporate a downstream flow deflector.

Figure 1:
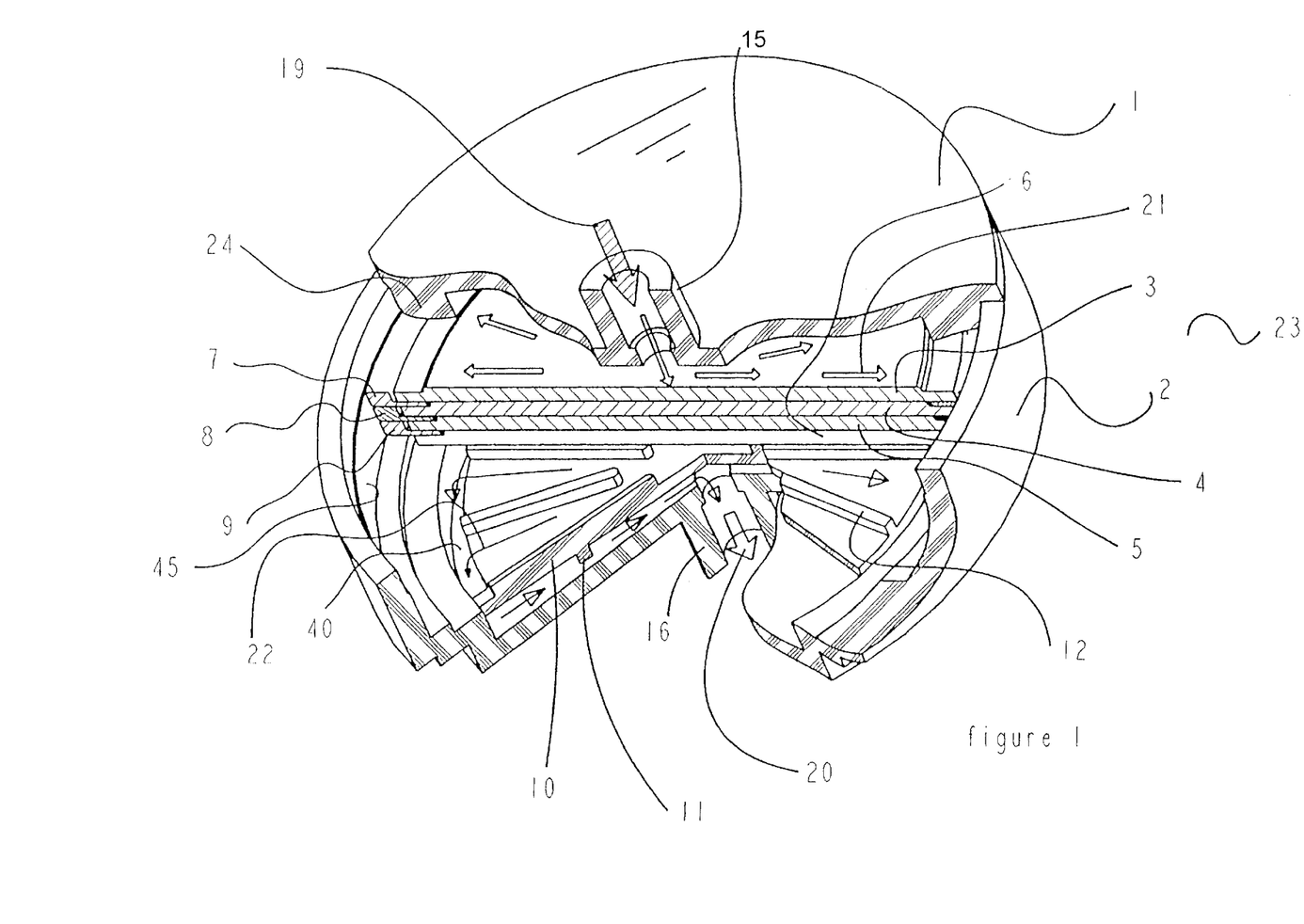
FIG. 1 depicts an isometric view with portions removed therefrom of a filtration device having a flow deflector in the second chamber thereof constructed in accordance with the principles of the present invention.
Figure 2:
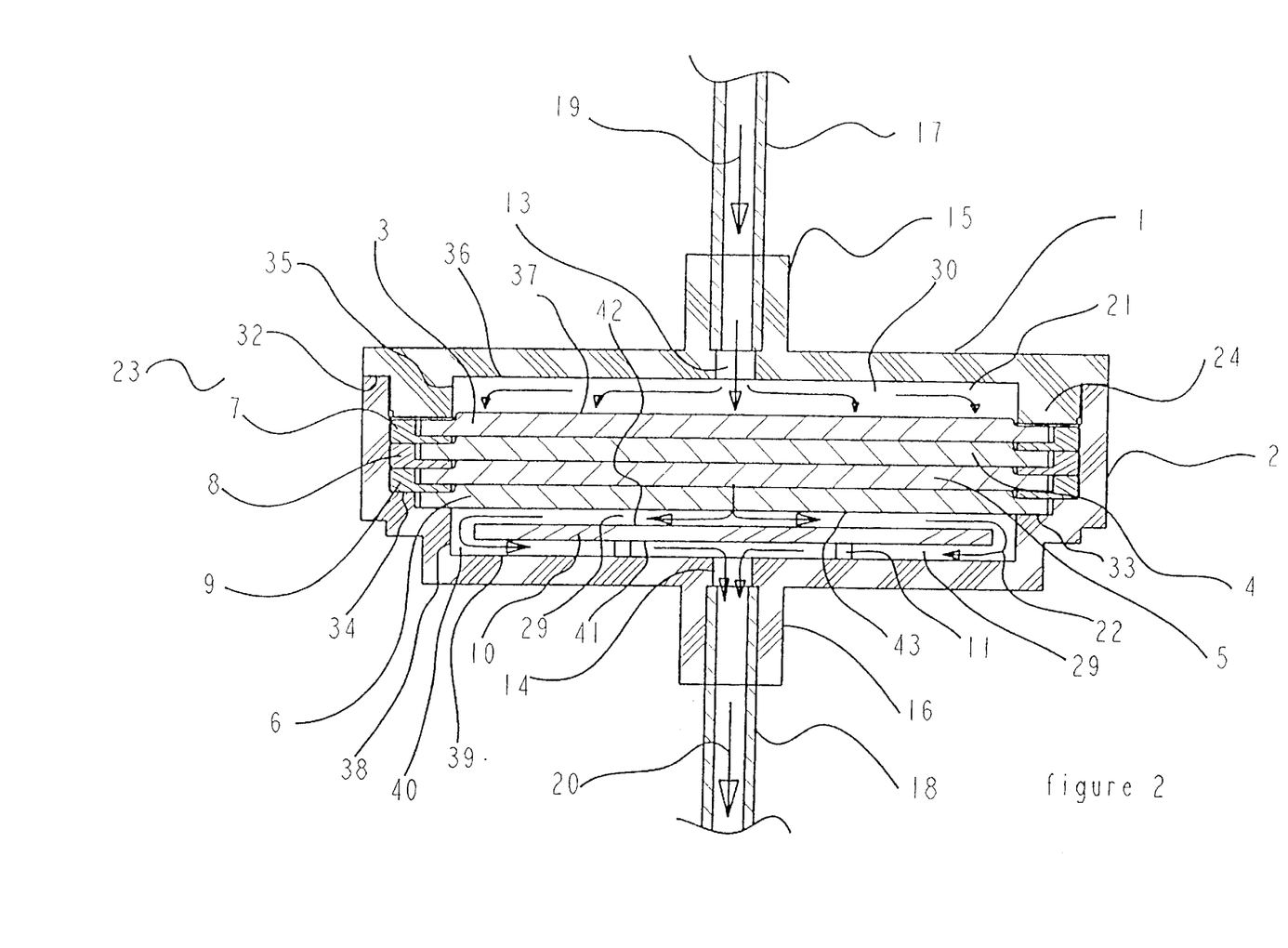
FIG. 2 depicts a sectional schematic representation of the filtration device of FIG. 1 depicting the flow of fluid therein and constructed and usable in accordance with the principles of the present invention.

Referring now specifically to the drawings, FIGS. 1 and 2 depict a filtration device, generally designated as 23, that comprises an inlet section 1, TCRF means, comprised of TCRF pads 3, 4, 5 and 6, seal rings 7, 8, 9 and flow deflector 10. Inlet section 1 is sealed to outlet section 2 at a joint 32 therebetween. Preferably the joint is sealed by ultrasonic weld, a heat weld, a solvent weld, a glue joint or any other means for creating a leak tight seal. TCRF pad 6 is sealed into the outlet section 2 by compression thereby forming a compression seal. The outer periphery of TCRF pad 6 is compressed between shelf 33 of outlet section 2 and a seal ring 9. TCRF pad 5, located on top of TCRF pad 6, is sealed into outlet section 2 using a compression seal. The outer periphery of TCRF pad 5 is compressed between seal ring 8 and seal ring 9. TCRF pad 4, located on top of TCRF pad 5, is sealed into outlet section 2 also using a compression seal. The outer periphery of TCRF pad 4 is compressed between seal ring 7 and seal ring 8. TCRF pad 3, located on top of TCRF pad 4, is also sealed into outlet half 2 using a compression seal. The outer periphery of TCRF pad 3 is compressed between seal ring 7 and the seal rib 24 protruding in the axial direction along the outer perimeter of inlet section 1. Seal rings 7, 8 and 9 are preferably press fit with wall 45 of outlet section 2. However, seal rings 7, 8 and 9 may be bonded to or into outlet section 2 using an ultrasonic weld, heat weld, solvent weld, glue or by using any other sealing means which will create a leak tight seal. If the seal rings are not press fitted into outlet section 2, then seal ring 9 could be bonded to outlet section 2 and the bottom surface of seal ring 8 could be bonded to the top surface of seal ring 9 and the bottom surface of seal ring 7 could be bonded to the top surface of seal ring 8. Although the device illustrated il FIGS. 1 and 2 includes four TCRF pads 3, 4, 5 and 6, the invention is not limited thereto and may include one or more TCRF pads.

The cavity 21 formed within the interior of the device 23 by the inside walls of inlet section 1 and outlet section 2 is divided into two chambers by TCRF pads 3, 4, 5 and 6. The upstream, upper or first chamber 30 is formed by wall 35 of inlet section 1, wall 36 of inlet section 1 and the upper surface 37 of TCRF pad 3. The downstream, lower or second chamber is formed by wall 38 of outlet section 2, wall 39 of outlet section 2 and the lower surface 43 of TCRF pad 6. The lower chamber 29 is divided into two sections by a flow deflector 10 within the lower chamber. The first section of lower chamber 29 is bounded by bottom surface 43 of TCRF pad 6 and top surface 42 of flow deflector 10. The second section of lower chamber 29 is bounded by bottom surface 41 of flow deflector 10 and by the surface 39 of outlet section 2.

Figure 3A:
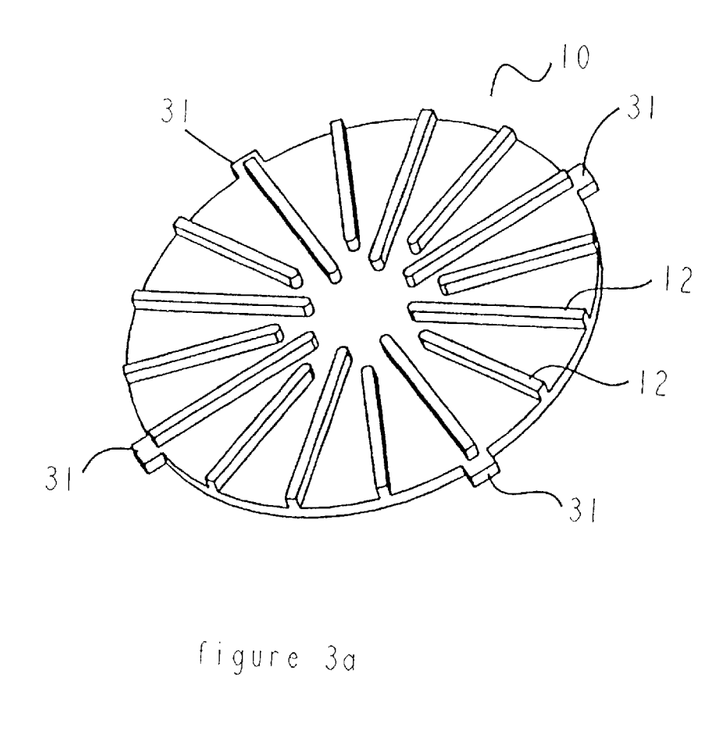
FIG. 3A depicts a top isometric view of the flow deflector used within the filtration device of FIGS. 1 and 2.
Figure 3B:
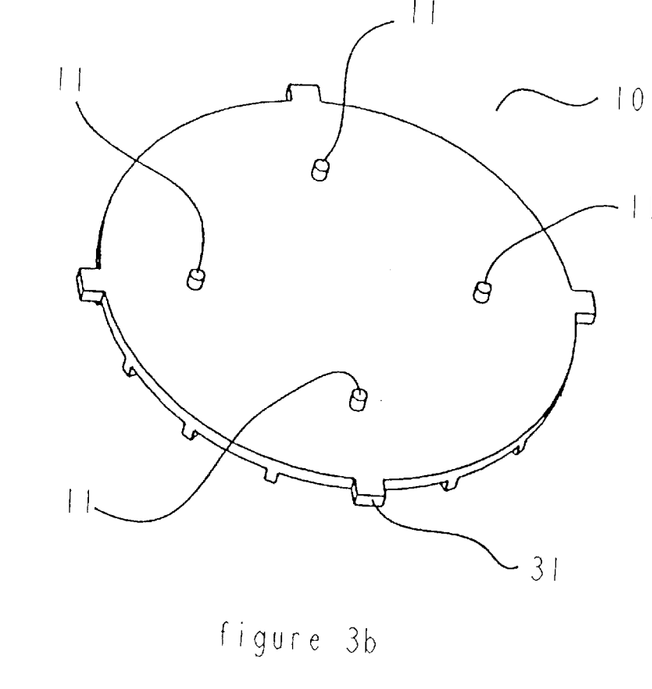
FIG. 3B depicts a bottom isometric view of tile flow deflector used within the filtration device of FIGS. 1 and 2.

Referring to FIGS. 3A and 3B, the flow deflector is formed of a thin disk which contains radial filter support ribs 12 on a first side thereof, alignment tabs 31 on the outer periphery, and support pins 11 on a second side thereof. The filter support ribs 12 function as a means for allowing radial flow of FSC product along the first side of the flow deflector. However, other means for allowing such a flow such as a series of support pins or a woven screen may be used in lieu of support ribs 12. The support pins 11 function as a means for supporting the flow deflector 10 above wall 39 of outlet section 2. The alignment tabs function as a means for positioning the flow deflector 10 within the lower chamber 29.

Figure 4:
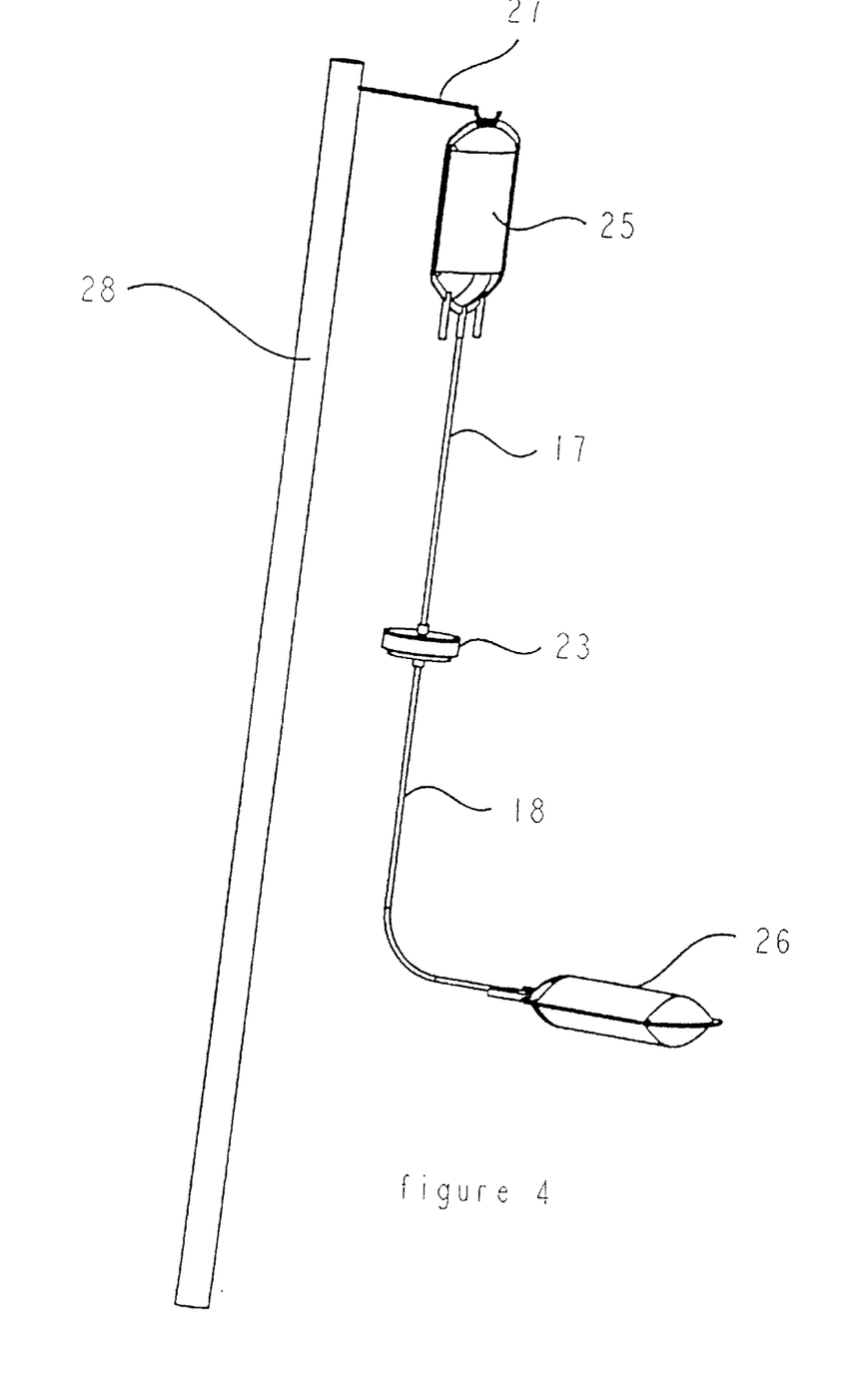
FIG. 4 depicts the filtration device of FIGS. 1 and 2 in an operational assembly with tubing, a supply bag and a recovery bag.

In FIG. 4 the filtration device 23 depicted ih FIG. 1 and FIG. 2 is in an operational assembly with inlet tube 17, outlet tube 18, supply bag 25 and recovery bag 26. Preferably, the user will obtain the assembly of FIG. 4 sterilized, without supply bag 25, with the inlet end of inlet tube 17 sealed to maintain system sterility. For performing filtration, inlet tube 17 (FIG. 2) attached to tube socket 15 at the center of the inlet section 1 would be bonded to a pigtail on supply bag 25, which contains a TCCSC product, using a sterile docking device as is well known in the art. Inlet tube 17 is in fluid flow relationship with upper chamber 30 via inlet port 13. Outlet tube 18, attached to a receiving bag, is bonded to outlet tube socket 16 located at the center of the outlet section 2. Outlet tube 18 is in fluid flow relationship with bottom chamber 29 via outlet port 14.

Filtration device 23 hangs in line. TCCSC product enters filtration device 23 from its inlet port 13 and FSC product exits filtration device 23 from its outlet port 14. In the process of filling filtration device 23 with TCCSC product, all of the air therein before the filtration process began is purged out of filtration device 23 through outlet tube 18 into receiving bag 26 before FSC product starts to flow out of filtration device 23. This process assures that little or no air gets trapped in TCRF pads 3, 4, 5 and 6. Therefore, the entire exposed surface area of the TCRF pads is used for filtration.

When filtering TCCSC product, the user would first close inlet tube 17 near the end to be attached to supply bag 25, with a tube clamp (not shown) and then make a sterile connection between the inlet end of inlet tube 17 and supply bag 25 using a sterile docking device as is well known in the art. The actual sterile connection is made between inlet tube 17 and a short length of tube which is a part of supply bag 25. The resulting system is illustrated in FIG. 4. Supply bag 25 may be suspended from an appropriate mechanism such as pole 28 with hook 27. Recovery bag 26 may be suspended by the mechanism or may rest oil a surface such as a bench top or the like.

Referring to FIGS. 1, 2 and 4, once the tube clamp (not shown) is opened, TCCSC product will begin to flow from supply bag 25 through inlet tube 17, through inlet port 13, into upper chamber 30. The air that was in inlet tube 17 will be forced ahead of the TCCSC product and into upper chamber 30. TCCSC product enters upper chamber 30 at the center, and as a result, upper chamber 30 is filled with TCCSC product from the center, then radially outward. This radial flow is illustrated by arrows in FIGS. 1 and 2. Because upper chamber 30 fills from the center and radially outward, TCRF pads 3, 4, 5, 6 will also wet from the center and radially outward. As upper chamber 30 becomes filled, any air remaining in upper chamber 30 will be forced out through the non-wet portions of TCRF pads 3, 4, 5 and 6, into lower chamber 29, through outlet port 14, through outlet tube 18, and into receiving bag 26. Upper chamber 30 should be sized in relation to the initial TCCSC product flow rate to assure that all of the air initially in upper chamber 30 will be forced out through TCRF pads 3, 4, 5 and 6. If the volume of upper chamber 30 in relation to the initial TCCSC product flow rate is too large, some air will become trapped in upper chamber 30.

As indicated, TCRF pads 3, 4, 5 and 6 wet radially outward and any air that was in them will be forced into lower chamber 29, through outlet port 14, through outlet tube 18, into receiving bag 26. Due to the radial outward wetting of TCRF pads 3, 4, 5 and 6, FSC product will first flow out of TCRF pad 6 from its center and then continue to flow out of TCRF pad 6 in a radial outward pattern. Thus, the first section of lower chamber 29 will also fill from its center radially outward. As the first section of lower chamber 29 fills, any air that had been forced out through TCRF pads 3, 4, 5 and 6 will also be forced radially outward through the first section of lower chamber 29.

Once the first section of lower chamber 29 is filled with FSC product, the FSC product will flow into the second section of lower chamber 29 radially inward, forcing air into the outlet port, and thereby venting air downstream. Once the second section of lower chamber 29 is filled with FSC product, outlet port 14 and outlet tube 18 will then be filled and finally, recovery bag 26. The flow around the flow deflector is illustrated by arrows in FIG. 2.

Due to the web matrix construction of TCRF pads 3, 4, 5 and 6, tumor cells will be retained within filter device 23 and the smaller stein cells and committed progenitor cells will pass through for recovery in recovery bag 26. The diameter of stem cells and committed progenitor cells ranges between about 5 and about 15 $\mu$m, while that of tumor cells ranges between about 20 and about 50 $\mu$m.

Preferably, the TCRF means provides at least a ten-fold reduction in tumor cells while also providing at least a 30% recovery of stem cells and preferably more than 50% recovery. The flow of stein cell product through the TCRF means should be at least 50 mL per hour. We have found that TCRF means having an air permeability of at least about 26.8 cubic feet per minute (CFM) (750 L/min) and more preferably, of about 118.5 CFM ($3.3 \times 10^3$ L/min) function well in the apparatus of the invention. TCRF means, such as the tumor cell reduction filter pads, having a higher air permeability are obtained with the use of cellulose or cellulose acetates that have a higher average surface area.

As collected SCP are frequently cryopreserved and stored for later use, it is important to note that the TCRF means will also retain any granulocytes that may be present in the contaminated stein cell product. This is advantageous because granulocytes will not survive the freezing rate of the filtered SCP and will lyse, releasing their intracellular contents into the supernatant solution, presumably resulting in the reduced viability of the stem cell product upon thawing. It is therefore desirable that granulocytes are removed prior to the cryopreservation process.

EXAMPLES

A preferred embodiment of the present invention is hereinafter described in more detail by means of the following examples which are provided by way of illustration and not by way of limitation.

Example 1

A model TCCSC product was prepared using blood mononuclear cells (BMNC) mixed with either adenocarcinoma or ductal carcinoma tumor cells (collectively, tumor cells, TC) in a 5:1 ratio. The composition was filtered in accordance with the principles of the present invention using cellulose or cellulose acetate-polyester composite TCRF pads 1.5 millimeters in thickness and having an effective pore size of 10 μm, with a variation from 5–150 μm, due to the web matrix construction of the TCRF pads. The FSC product was analyzed for BMNC and TC content. Wright-Giemsa stained cytospins revealed that the recovery of BMNC was 25–60 fold higher than that of TC.

Example 2

A model TCCSC product was prepared wherein the BMNC to TC ratio was 50:1. To facilitate an accurate reading of the results, the TC were pre-labeled with a fluorescent membrane dye. The TCCSC product was filtered using the same cellulose-acetate TCRF pads as in Example 1 and upon analysis of the FSC product, the concentration of TC was undetectable, indicating at least a 30-fold preferential retention of TC.

Furthermore, because stem cells are smaller than BMNC, post-filtration recovery of granulocytes/macrophages and erythroid progenitor cells should necessarily be greater than that of BMNC. In fact, the filtration of TC-free BMNC revealed that the concentration of hematopoietic stem cells in the recovered product was almost 10-fold higher than in the unfiltered product; indicating that approximately 80% of all fully viable hematopoietic precursors can be recovered under conditions that reduce the concentration of TC 30-fold, values comparable to those obtained with currently used TC reduction processes that rely oil positive selection.

Table 1 provides the results of Examples 1 and 2.

TABLE 1

| STARTING RATIO BMNC:TC | LOG REDUCTION TC | LOG REDUCTION BMNC |
|---|---|---|
| NO TC | NA | 1.1 |
| 5:1 | 2.2, 2.8 | 0.8, 1.0 |
| 50:1 | >1.5 | 0.6 |

Example 3

A model TCCSC product was prepared in which the BMNC to TC ratio was 10:1. Several filtration tests of the composition were conducted, using various TCRF pad media. Following filtration, the FSC product was analyzed for the percentage of total cells recovered, the ratio of BMNC:TC, the type of cells recovered and the fold increase in concentration of a specific hematopoietic colony forming cell, CFU-GM (a granulocyte/macrophage precursor).

The results of these filtration tests ("A"–"V") are reflected in Tables 2 and 2A. As can be seen, optimal results were obtained in Test "U" wherein two TCRF pads, characterized as TCRF pad media Stemi Cell-3 (SC-3) were utilized. In this case, 14.9% of total BMNC were recovered, with an 8.7 fold increase in the concentration of CFU-GM.

TABLE 2

| TEST | AIR PERMEABILITY CU FT/MIN | TCRF PAD MEDIA | NO. OF PADS USED | % TOTAL CELL YIELD |
|---|---|---|---|---|
| A | 3–4 | LEUKONET ™ | 2 | 1.06 |
| B | 3–4 | LEUKONET ™ | 4 | 0.40 |
| C | 3–4 | MILLIPORE 4528-41 | 2 | 1.90 |
| D | 3–4 | MILLIPORE 4528-41 | 4 | 1.50 |
| E | 3–4 | MILLIPORE 4528-41 | 2 | 3.00 |
| F | 3–4 | MILLIPORE 4528-41 | 4 | 2.45 |
| G | 31 | LYDALL LB ™ 170-54-D | 2 | 20.0 |
| H | 31 | LYDALL LB ™ 170-54-D | 4 | 5.20 |
| I | 3–4 | BIOCMPTBL 2 MG/UL | 2 | 1.20 |
| J | 3–4 | BIOCMPTBL 2 MG/UL | 4 | 1.00 |
| K | 3–4 | BIOCMPTBL 5 MG/UL | 2 | 2.20 |
| L | 3–4 | BIOCMPTBL 5 MG/UL | 4 | 2.00 |
| M | 3–4 | BIOCMPTBL 10 MG/UL | 2 | 2.00 |
| N | 3–4 | BIOCMPTBL 10 MG/UL | 4 | 1.00 |
| O | 31 | LYDALL LB ™ 170-64-D | 2 | 4.60 |
| P | 31 | LYDALL LB ™ 170-64-D | 4 | 0.40 |
| Q | 26.8–30.5 | SC-1 | 2 | 5.00 |
| R | 26.8–30.5 | SC-1 | 4 | 1.30 |
| S | 43.6–44.1 | SC-2 | 2 | 9.04 |
| T | 43.6–44.1 | SC-2 | 4 | 5.00 |
| U | 118.5 | SC-3 | 2 | 14.9 |
| V | 118.5 | SC-3 | 4 | 9.00 |

TABLE 2A

| TEST | PRE-FILTER RATIO BMNC:TC | POST-FILTER RATIO BMNC:TC | POST-FILTER CELL TYPES | POST-FILTER FOLD INCREASE CFU-GM |
|---|---|---|---|---|
| A | 10:1 | >100:1 | MRBC | — |
| B | 10:1 | >100:1 | MRBC | — |
| C | 10:1 | >100:1 | MRBC | — |
| D | 10:1 | >100:1 | MRBC | — |
| E | 10:1 | >100:1 | MRBC | — |
| F | 10:1 | >100:1 | MRBC | — |
| G | 10:1 | >100:1 | MRBC LMPHCT MCRPHG | 1 |
| H | 10:1 | >100:1 | MRBC LMPHCT MCRPHG | 1 |
| I | 10:1 | >100:1 | MRBC | — |
| J | NA | NA | MRBC | — |
| K | NA | NA | MRBC | — |
| L | NA | NA | MRBC | — |
| M | NA | NA | MRBC LMPHCT MCRPHG | 0 |
| N | NA | NA | MRBC LMPHCT MCRPHG | 0 |
| O | 10:1 | >100:1 | MRBC LMPHCT MCRPHG | 0 |
| P | 10:1 | >100:1 | MRBC LMPHCT MCRPHG | 0 |

TABLE 2A-continued

| TEST | PRE-FILTER RATIO BMNC:TC | POST-FILTER RATIO BMNC:TC | POST-FILTER CELL TYPES | POST-FILTER FOLD INCREASE CFU-GM |
|---|---|---|---|---|
| Q | NA | NA | MRBC LMPHCT MCRPHG | 2.4 |
| R | NA | NA | MRBC LMPHCT MCRPHG | 1.7 |
| S | NA | NA | MRBC LMPHCT MCRPHG | 4.0 |
| T | NA | NA | MRBC LMPHCT MCRPHG | 3.0 |
| U | NA | NA | MRBC LMPHCT MCRPHG | 8.7 |
| V | NA | NA | MRBC LMPHCT MCRPHG | 3.7 |

NA = TC growing too slowly to provide adequate cells for trials
MRBC = Mature Red Blood Cells
LMPHCT = Lymphocytes
MCRPHG = Macrophages
MEDIA = TCRF pads were made by various manufacturers. Leukonet ™ and Lydall pads were prepared from the same filter material, available from Lydall, Inc. (Manchester, CT). The material comprised polyester fibers, cellulose fibrils and NW-1845, an acrylic binder (Rohm and Haas). The polyester fibers had an average denier of 0.5 mm in each filter pad, except SC-3, where the polyester fibers had an average denier of 1.5 mm. The cellulose fibrils had a surface area of about 20 m$^2$/g.

The various Lydall pads were obtained by varying the percentage of polyester fibers in the material. This is shown in Table 2 as a function of air permeability, which was determined by the Frasier method employing a head pressure of 12.7 kg/M$^2$.

The Millipore TCRF pad was a Leukonet™ TCRF pad coated with a hydrophilic polymer formed of a cross-linked hydroxyalkyl acrylate according to the method of U.S. Pat. No. 4,618,533, issued Oct. 21, 1986 to Steuck and assigned to Millipore Corp. (Bedford, Mass.). The Biocmptbl TCRF pad was a Leukonet™ TCRF pad coated with various concentrations of phosplhoryl choline. (Biocompatibles, Ltd., Middlesex, England)

While the present invention is not intended to be limited to the use of TCRF pads as the TCRF means, nor by the specific number of TCRF pads used during a single filtration, optimal tumor cell retention and stern cell recovery has been obtained with the concurrent use of two TCRF pads.

This invention has been described in terms of specific embodiments, set forth in detail. It should, however, be understood that the embodiments are presented by way of illustration only, and the invention is not limited thereto. Modifications and variations within the spirit and scope of the claims that follow will be readily apparent from this disclosure, as those skilled in the art will appreciate.

We claim:

1. A method for removing tumor cells from a tumor cell-contaminated stem cell product, comprising the steps of:
    (a) providing an in-line filtration device including:
        a housing having an inlet port and an outlet port therein; and
        a tumor cell reduction filter means disposed within said housing between the inlet port and the outlet port so as to filter tumor cell-contaminated stem cell products which flow into the filtration device via the inlet port, said tumor cell reduction filter means dividing said housing into a first chamber and a second chamber;
    (b) providing a tumor cell-contaminated stem cell product;
    (c) passing the tumor cell-contaminated stem cell product through the filtration device wherein tumor cells are retained by the tumor cell reduction filter means within the filtration device and the stem cell product passes through the tumor cell reduction filter means and out of the filtration device; and
    (d) recovering a tumor cell-depleted stem cell product, wherein said tumor cell reduction filter means provides at least a ten-fold reduction in tumor cells and at least a 30% recovery of stem cells.

2. THe method of claim 1 wherein the filtration device further includes means, disposed within the filtration device, for allowing gases to vent from the filtration device through the outlet port.

3. The method of claim 1 wherein the filter means provides a stem cell product flow rate of at least 50 mL per hour.

4. The method of claim 1 wherein the filter means comprises one or more tumor cell reduction filter pads.

5. The method of claim 1 wherein tile filter means has an air permeability of at least about 750 L/min.

6. The method of claim 5 wherein the filter means has an air permeability of at least about 3.3×10$^3$ L/min.

7. The method of claim 1 wherein the tumor cell-contaminated stem cell product comprises a stem cell product contaminated with tumor cells selected from the group consisting of ovarian cancer cells, testicular cancer cells, breast cancer cells, multiple myeloma cells, non-Hodgkin's lymphoma cells, chronic myelogenous leukemia cells, chronic lymphocytic leukemia cells, acute myeloid leukemia cells, and acute lymphocytic leukemia cells.

8. Tile method of claim 1 wherein the tumor cell-contaminated stem cell product comprises a stem cell product contaminated with tumor cells selected from the group consisting of ductal carcinoma cells and adenocarcinoma cells.

9. A tumor cell reduction filter means suitable for use in an in-line filtration device, the tumor cell reduction filter means comprising a mechanically stable substrate that provides at least a ten-fold reduction in tumor cells and at least a 30% recovery of stem cells in a filtered stem cell product.

10. The filter means of claim 9 further characterized in that the filter means provides a stem cell product flow rate of at least 50 mL per hour.

11. The filter means of claim 9 further characterized in that the filter means comprises one or more tumor cell reduction filter pads having a web matrix construction comprised of a plurality of fibers and fibrils.

12. The filter means of claim 11 wherein the fibers are formed from polyester having a denier of about 1.5 inm and the fibrils are formed of cellulose.

13. The filter means of claim 9 further characterized in that the filter means has an air permeability of at least about 750 L/min.

14. The filter means of claim 13 further characterized in that the filter means has an air permeability of at least about 3.3×10$^3$ L/min.

15. An apparatus suitable for use as a filtration device for removing tumor cells from a tumor cell-contaminated stem cell product, the filtration device comprising:

a housing having an inlet port and an outlet port therein; and a tumor cell reduction filter means disposed within the housing between the inlet port and the outlet port so as to filter tumor cell-contaminated stem cell products which flow into the housing via the inlet port, the filter means dividing said housing into a first chamber and a second chamber, and wherein said tumor cell reduction filter means provides at least a ten-fold reduction in tumor cells and at least a 30% recovery of stem cells in a filtered stem cell product.

16. The filtration device of claim 15 further including means, disposed within the housing, for allowing gases to vent from the housing through the outlet port.

17. The filtration device of claim 15 wherein the filter means provides a stem cell product flow rate of at least 50 mL per hour.

18. The filtration device of claim 15 wherein the filter means comprises one or more tumor cell reduction filter pads.

19. The filtration device of claim 15 wherein the filter means has an air permeability of at least about 750 L/min.

20. The filtration device of claim 19 wherein the filter means has an air permeability of at least about $3.3 \times 10^3$ L/min.

* * * * *

UNITED STATES PATENT AND TRADEMARK OFFICE
CERTIFICATE OF CORRECTION

PATENT NO. : 6,177,019

DATED : January 23, 2001

INVENTOR(S) : Castino, et al.

It is certified that error appears in the above-identified patent and that said Letters Patent is hereby corrected as shown below:

Col. 12, Claim 12, line 57    delete "inm" and replace with -- mm --

Signed and Sealed this

Fifteenth Day of May, 2001

*Attest:*

NICHOLAS P. GODICI

*Attesting Officer*    Acting Director of the United States Patent and Trademark Office